US010687716B2

(12) United States Patent
Goldshtein et al.

(10) Patent No.: US 10,687,716 B2
(45) Date of Patent: Jun. 23, 2020

(54) DRIFT COMPENSATION FOR IMPLANTED CAPACITANCE-BASED PRESSURE TRANSDUCER

(71) Applicant: VECTORIOUS MEDICAL TECHNOLOGIES LTD., Tel Aviv (IL)

(72) Inventors: Oren Goldshtein, Nahariya (IL); Shmuel Livne, Yehud (IL)

(73) Assignee: VECTORIOUS MEDICAL TECHNOLOGIES LTD., Tel Aviv (IL)

( * ) Notice: Subject to any disclaimer, the term of this patent is extended or adjusted under 35 U.S.C. 154(b) by 0 days.

(21) Appl. No.: 14/437,198

(22) PCT Filed: Nov. 10, 2013

(86) PCT No.: PCT/IB2013/060038
§ 371 (c)(1),
(2) Date: Apr. 21, 2015

(87) PCT Pub. No.: WO2014/076620
PCT Pub. Date: May 22, 2014

(65) Prior Publication Data
US 2015/0282720 A1    Oct. 8, 2015

Related U.S. Application Data

(60) Provisional application No. 61/726,022, filed on Nov. 14, 2012.

(51) Int. Cl.
*A61B 5/03* (2006.01)
*A61B 5/0215* (2006.01)
(Continued)

(52) U.S. Cl.
CPC ........ *A61B 5/02156* (2013.01); *A61B 5/0215* (2013.01); *A61B 5/02133* (2013.01);
(Continued)

(58) Field of Classification Search
CPC ............... G01L 9/0072; A61B 5/02156; A61B 2562/0247
See application file for complete search history.

(56) References Cited

U.S. PATENT DOCUMENTS 3,264,861 A    8/1966  Miles
4,127,110 A   11/1978  Bullara
(Continued)

FOREIGN PATENT DOCUMENTS

JP      S5973747 A      4/1984
KR   20040060577 A      7/2004
(Continued)

OTHER PUBLICATIONS

International Application # PCT/IB2015/060054 Search Report dated Mar. 21, 2016.
(Continued)

*Primary Examiner* — Devin B Henson
*Assistant Examiner* — H. Q. Nguyen
(74) *Attorney, Agent, or Firm* — Kligler & Associates Patent Attorneys Ltd (57) ABSTRACT

A method includes, in a living organ (28) in which an ambient pressure varies as a function of time, sensing the ambient pressure using a pressure sensor (36, 90, 174), which has a capacitance that varies in response to the ambient pressure, so as to produce a time-varying waveform. A calibration voltage, which modifies the capacitance and thus the time-varying waveform, is applied to the pressure sensor. The time-varying waveform is processed so as to isolate and measure a contribution of the calibration
(Continued)

voltage to the waveform. A dependence of the capacitance on the ambient pressure is calibrated using the measured contribution of the calibration voltage.

31 Claims, 6 Drawing Sheets

(51) Int. Cl.
*A61B 5/00* (2006.01)
*A61B 5/021* (2006.01)

(52) U.S. Cl.
CPC ............ *A61B 5/036* (2013.01); *A61B 5/6869* (2013.01); *A61B 5/0031* (2013.01); *A61B 2560/0223* (2013.01); *A61B 2560/0228* (2013.01); *A61B 2562/028* (2013.01); *A61B 2562/0247* (2013.01)

(56) References Cited

U.S. PATENT DOCUMENTS

| | | | |
|---|---|---|---|
| 4,206,761 A | 6/1980 | Cosman | |
| 4,237,900 A | 12/1980 | Ritchie et al. | |
| 4,256,094 A | 3/1981 | Kapp et al. | |
| 4,377,851 A | 3/1983 | McNamara | |
| 4,432,372 A | 2/1984 | Monroe | |
| 4,519,401 A | 5/1985 | Ko et al. | |
| 4,743,836 A | 5/1988 | Grzybowski et al. | |
| 4,791,934 A | 12/1988 | Brunnett | |
| 4,881,939 A | 11/1989 | Newman | |
| 5,105,190 A | 4/1992 | Kip et al. | |
| 5,113,868 A | 5/1992 | Wise et al. | |
| 5,480,412 A | 1/1996 | Mouchawar et al. | |
| 5,493,470 A | 2/1996 | Zavracky et al. | |
| 5,514,171 A | 5/1996 | Hoegnelid et al. | |
| 5,549,646 A * | 8/1996 | Katz .................... | A61N 1/3706 607/4 |
| 5,564,434 A * | 10/1996 | Halperin .............. | A61B 5/0031 600/488 |
| 5,942,692 A | 8/1999 | Haase et al. | |
| 6,015,386 A | 1/2000 | Kensey et al. | |
| 6,025,725 A | 2/2000 | Gershenfeld et al. | |
| 6,051,853 A | 4/2000 | Shimada et al. | |
| 6,111,520 A | 8/2000 | Allen et al. | |
| 6,113,553 A | 9/2000 | Chubbuck | |
| 6,171,252 B1 | 1/2001 | Roberts | |
| 6,275,681 B1 | 8/2001 | Vega et al. | |
| 6,309,350 B1 | 10/2001 | VanTassel et al. | |
| 6,389,371 B1 | 5/2002 | Tsuchiya et al. | |
| 6,409,674 B1 | 6/2002 | Brockway et al. | |
| 6,622,041 B2 | 9/2003 | Terry, Jr. et al. | |
| 6,667,725 B1 | 12/2003 | Simons et al. | |
| 6,772,070 B2 | 8/2004 | Gilmanshin et al. | |
| 6,778,070 B1 | 8/2004 | Thomas | |
| 6,926,670 B2 | 8/2005 | Rich et al. | |
| 6,936,053 B1 | 8/2005 | Weiss | |
| 7,086,270 B2 | 8/2006 | Weinberg et al. | |
| 7,149,587 B2 | 12/2006 | Wardle et al. | |
| 7,216,048 B2 | 5/2007 | Wang et al. | |
| 7,256,695 B2 | 8/2007 | Hamel et al. | |
| 7,317,951 B2 | 1/2008 | Schneider et al. | |
| 7,335,161 B2 | 2/2008 | Von Arx et al. | |
| 7,413,547 B1 | 8/2008 | Lichtscheidl et al. | |
| 7,425,749 B2 | 9/2008 | Hartzell et al. | |
| 7,509,169 B2 | 3/2009 | Eigler et al. | |
| 7,515,971 B1 | 4/2009 | Doan | |
| 7,628,054 B2 | 12/2009 | Hajishah et al. | |
| 7,634,319 B2 | 12/2009 | Schneider et al. | |
| 7,635,338 B2 | 12/2009 | Eide | |
| 7,647,831 B2 | 1/2010 | Corcoran et al. | |
| 7,677,107 B2 | 3/2010 | Nunez et al. | |
| 7,678,123 B2 | 3/2010 | Chanduszko | |
| 7,684,872 B2 | 3/2010 | Carney et al. | |
| 7,686,768 B2 | 3/2010 | Bodecker et al. | |
| 7,762,138 B2 | 7/2010 | Zdeblick et al. | |
| 7,860,579 B2 | 12/2010 | Goetzinger et al. | |
| 7,899,550 B1 | 3/2011 | Doan et al. | |
| 8,021,307 B2 | 9/2011 | White et al. | |
| 8,118,749 B2 | 2/2012 | White et al. | |
| 8,154,389 B2 | 4/2012 | Rowland et al. | |
| 8,285,204 B2 | 10/2012 | Martin | |
| 8,353,841 B2 | 1/2013 | White et al. | |
| 8,355,777 B2 | 1/2013 | White et al. | |
| 8,406,358 B1 | 3/2013 | Uehara et al. | |
| 8,432,265 B2 | 4/2013 | Rowland et al. | |
| 8,493,187 B2 | 7/2013 | Rowland et al. | |
| 8,810,405 B2 | 8/2014 | Stevenson et al. | |
| 8,894,582 B2 | 11/2014 | Nunez et al. | |
| 9,513,609 B2 | 12/2016 | Thueringer et al. | |
| 9,662,066 B2 | 5/2017 | Ledet et al. | |
| 9,730,764 B2 | 8/2017 | Van Der Weide et al. | |
| 2001/0018596 A1 | 8/2001 | Selmon et al. | |
| 2002/0045921 A1 | 4/2002 | Wolinsky et al. | |
| 2002/0077556 A1 | 6/2002 | Schwartz | |
| 2002/0120200 A1 | 8/2002 | Brockway et al. | |
| 2003/0097073 A1 | 5/2003 | Bullister et al. | |
| 2003/0139677 A1 | 7/2003 | Fonseca et al. | |
| 2004/0103906 A1 | 6/2004 | Schulman et al. | |
| 2004/0158167 A1 * | 8/2004 | Smith .................... | A61B 5/053 600/547 |
| 2005/0004644 A1 | 1/2005 | Kelsch et al. | |
| 2005/0065589 A1 | 3/2005 | Schneider et al. | |
| 2005/0088184 A1 | 4/2005 | Burdick et al. | |
| 2005/0288596 A1 | 12/2005 | Eigler et al. | |
| 2006/0116572 A1 | 6/2006 | Case | |
| 2006/0161364 A1 * | 7/2006 | Wang .................... | G01L 27/002 702/98 |
| 2006/0206178 A1 | 9/2006 | Kim | |
| 2006/0229488 A1 | 10/2006 | Ayre et al. | |
| 2006/0287602 A1 | 12/2006 | O'Brien et al. | |
| 2007/0049980 A1 | 3/2007 | Zielinski et al. | |
| 2007/0049984 A1 | 3/2007 | Osypka | |
| 2007/0118038 A1 | 5/2007 | Bodecker et al. | |
| 2007/0135826 A1 | 6/2007 | Zaver et al. | |
| 2007/0142727 A1 | 6/2007 | Zhang et al. | |
| 2007/0179583 A1 | 8/2007 | Goetzinger et al. | |
| 2007/0255144 A1 | 11/2007 | Tulkki et al. | |
| 2007/0261496 A1 | 11/2007 | Jonsson et al. | |
| 2007/0293779 A1 | 12/2007 | Bardy | |
| 2008/0004673 A1 | 1/2008 | Rossing et al. | |
| 2008/0033527 A1 | 2/2008 | Nunez et al. | |
| 2008/0045242 A1 | 2/2008 | Dekock et al. | |
| 2008/0064966 A1 | 3/2008 | Brockway et al. | |
| 2008/0092663 A1 | 4/2008 | Corcoran et al. | |
| 2008/0139959 A1 | 6/2008 | Miethke et al. | |
| 2008/0154101 A1 | 6/2008 | Jain et al. | |
| 2008/0227487 A1 | 9/2008 | Daniels et al. | |
| 2008/0269573 A1 | 10/2008 | Najafi et al. | |
| 2008/0281212 A1 | 11/2008 | Nunez et al. | |
| 2009/0005859 A1 | 1/2009 | Keilman | |
| 2009/0013791 A1 | 1/2009 | Zdeblick et al. | |
| 2009/0024042 A1 | 1/2009 | Nunez et al. | |
| 2009/0030291 A1 | 1/2009 | O'Brien et al. | |
| 2009/0036754 A1 | 2/2009 | Pons et al. | |
| 2009/0069648 A1 | 3/2009 | Irazogui et al. | |
| 2009/0093729 A1 | 4/2009 | Zhang et al. | |
| 2009/0192381 A1 | 7/2009 | Brockway et al. | |
| 2009/0275924 A1 | 11/2009 | Lattanzio et al. | |
| 2009/0281520 A1 | 11/2009 | Highley et al. | |
| 2009/0299216 A1 | 12/2009 | Chen et al. | |
| 2010/0179449 A1 | 7/2010 | Chow et al. | |
| 2010/0179618 A1 | 7/2010 | Marnfeldt et al. | |
| 2010/0249756 A1 | 9/2010 | Koh | |
| 2010/0280330 A1 | 11/2010 | Samuelsson et al. | |
| 2011/0021887 A1 | 1/2011 | Crivelli et al. | |
| 2011/0040206 A1 | 2/2011 | Burger et al. | |
| 2011/0043336 A1 | 2/2011 | Gueorguiev | |
| 2011/0133894 A1 | 6/2011 | Hennig et al. | |
| 2011/0160560 A1 | 6/2011 | Stone | |
| 2011/0264217 A1 | 10/2011 | Qureshi | |
| 2011/0303229 A1 | 12/2011 | Najafi et al. | |
| 2012/0022507 A1 | 1/2012 | Najafi et al. | |
| 2012/0319862 A1 | 12/2012 | Nagy et al. | |

(56) References Cited

U.S. PATENT DOCUMENTS

| | | |
|---|---|---|
| 2013/0107913 A1 | 5/2013 | Savoj |
| 2013/0215979 A1 | 8/2013 | Yakovlev et al. |
| 2013/0222153 A1 | 8/2013 | Rowland et al. |
| 2013/0233086 A1 | 9/2013 | Besling et al. |
| 2014/0028467 A1 | 1/2014 | Nagy et al. |
| 2014/0062717 A1 | 3/2014 | Mudumbai et al. |
| 2014/0155710 A1 | 6/2014 | Rowland et al. |
| 2014/0306807 A1 | 10/2014 | Rowland et al. |
| 2015/0290465 A1 | 10/2015 | Mashiach |
| 2016/0058324 A1 | 3/2016 | Cao et al. |
| 2017/0018172 A1 | 1/2017 | He et al. |
| 2017/0118543 A1 | 4/2017 | Ha et al. |
| 2017/0155429 A1 | 6/2017 | Hung et al. |

FOREIGN PATENT DOCUMENTS

| | | |
|---|---|---|
| WO | 2006042280 A2 | 4/2006 |
| WO | 2008042229 A2 | 4/2008 |
| WO | 2008127525 A1 | 10/2008 |
| WO | 2009097485 A1 | 8/2009 |
| WO | 2011053246 A1 | 5/2011 |
| WO | 2012078861 A2 | 6/2012 |
| WO | 2012090206 A2 | 7/2012 |
| WO | 2014006471 A2 | 1/2014 |
| WO | 2014145012 A2 | 9/2014 |
| WO | 2014170771 A1 | 10/2014 |

OTHER PUBLICATIONS

Cleven et al., "A Novel Fully Implantable Wireless Sensor System for Monitoring Hypertension Patients", IEEE Transactions on Biomedical Engineering vol. 59, No. 11, pp. 3124-3130, Nov. 2012.

Jiang., "Design challenges of implantable pressure monitoring system", Frontiers of Neuroscience, vol. 4, Art 29, pp. 1-4, Feb. 26, 2010.

Simons et al., "Spiral chip implantable radiator and printed loop external receptor for RF telemetry in bio-sensor systems", In Radian and Wireless Conference IEEE, 12 pages, 2004.

Simons et al., "Wearable wireless telemetry system for implantable bio-Mems sensors", In Engineering in Medicine and Biology Society Conference, IEEE, 12 pages, 2006.

Maxim, "Approaches for Compensating Span and Offset in Pressure Sensors", Application Note 743, 5 pages, Mar. 27, 2001.

Coosemans., "An autonomous bladder pressure monitoring system", Katholike Universiteit Leuven, Department ESAT-MICAS, Kasteelpark Arenberg, Belgium, Sensors and Actuators A: Physical, Elsevier BV, vol. 123-124, pp. 155-161, Sep. 23, 2005.

Dai et al., "Capacitive Micro Pressure Sensor integrated with a Ring Oscillator Circuit on Chip", Sensors 2009, vol. 9, Chapter 12, pp. 10158-10170, Jan. 1, 2009.

European Application # 14785775.9 Search Report dated Oct. 24, 2016.

JP Application # 2015-541286 Office Action dated Mar. 8, 2017.

International Application # PCT/IB2013/060038 Search Report dated May 1, 2014.

Yameogo et al., "Self Calibrating pressure sensor for biomedical applications", IEEE Sensors Conference, pp. 691-694, Oct. 25-28, 2009.

Goldshtein et al., U.S. Appl. No. 14/766,750, filed Aug. 9, 2015.

International Application # PCT/IB2014/060085 Search Report dated Jul. 8, 2014.

Olivo et al., "Electronic implants: Power delivery and management", Integrated Systems Laboratory—EPFL, 6 pages, Mar. 22, 2013.

Mandal et al., "Power-Efficient Impedance-Modulation Wireless Data Links for Biomedical Implants", IEEE Transactions on Biomedical Circuits and Systems, vol. 2, No. 4, pp. 301-315, Dec. 4, 2008.

Bradford et al., "Wireless Power and Data Transmission for a Pressure Sensing Medical Implant", Proceedings BMT 2010, Rostock, Germany, 4 pages, Oct. 6-8, 2010.

Zaie et al., "An Implantable Microsystem for Tonometric Blood Pressure Measurement", Biomedical Microdevices, vol. 3, Issue 4, pp. 285-292, Dec. 2001.

U.S. Appl. No. 14/766,750 office action dated Feb. 23, 2018.

European Application # 13855953.9 office action dated Aug. 18, 2017.

European Application # 13855953.9 search report dated May 30, 2016.

* cited by examiner

DRIFT COMPENSATION FOR IMPLANTED CAPACITANCE-BASED PRESSURE TRANSDUCER

CROSS-REFERENCE TO RELATED APPLICATIONS

This application claims the benefit of U.S. Provisional Patent Application 61/726,022, filed Nov. 14, 2012, whose disclosure is incorporated herein by reference.

FIELD OF THE INVENTION

The present invention relates generally to pressure transducers, and particularly to calibration of pressure transducers.

BACKGROUND OF THE INVENTION

Sensory implants are used for monitoring physiological parameters of patients, such as for measuring blood pressure in a cardiac chamber. Various types of sensory implants and associated methods are known in the art. For example, U.S. Patent Application Publication 2007/0261496, whose disclosure is incorporated herein by reference, describes biological fluid device that comprises a pressure sensor. The pressure sensor comprises a compressible container, the compression of which is indicative of the pressure, and is capable of wireless communication.

U.S. Pat. No. 7,335,161, whose disclosure is incorporated herein by reference, describes an implantable cardiac device that is configured and programmed to collect blood pressure waveforms from one or more implantable pressure sensors. Techniques are described for extracting features and reducing noise in the pressure waveforms by averaging waveforms which are aligned with a detected cardiac cycle. Noise can also be reduced by gating and calibration functions performed in accordance with other sensor data.

U.S. Pat. No. 5,942,692, whose disclosure is incorporated herein by reference, describes a capacitive pressure sensor that includes a chamber coupled to a region whose pressure is to be determined. The sensor includes a conductive flexible diaphragm and a pair of electrodes, each defining a capacitance with the diaphragm. Variations in pressure in the chamber cause deflection of the diaphragm which in turn causes variation in the capacitances. A processing circuit applies an excitation signal to the capacitances and couples the capacitances to inductive elements. A current through the inductive elements is detected to determine the difference in the sensor capacitances and, therefore, the deflection of the diaphragm and the pressure in the chamber.

U.S. Patent Application Publication 2007/0142727, whose disclosure is incorporated herein by reference, describes a cardiovascular pressure data analyzing system having one or more implanted pressure sensors, an implanted communication device in wireless communication with the sensor and an external data processing unit adapted to use real-time barometric data to calibrate uncalibrated pressure data received from the communication device. The external data processing unit can be portable, is in communication with a remote database to transfer the calibrated pressure data to the remote database, and is capable of providing reprogramming information to the communication device. A method for analyzing pressure data includes gathering pressure data from an implanted pressure sensor in a human body, retrieving the pressure data through a communication device implanted in the human body, transmitting pressure data from the communication device to an external data processing unit, and calibrating the pressure data at the external processing unit to compensate for inherent characteristics of the sensor.

U.S. Patent Application Publication 2011/0160560, whose disclosure is incorporated herein by reference, describes an implantable pressure sensor system having a sensor assembly configured and adapted to measure pressure in a volume. The sensor assembly includes at least a first MEMS pressure sensor, an application-specific integrated circuit (ASIC) having memory means, temperature compensation system, drift compensation system, and power supply means for powering the sensor assembly. The first MEMS pressure sensor has a pressure sensing element that is responsive to exposed pressure, the pressure sensing element being adapted to generate a pressure sensor signal representative of the exposed pressure. The temperature compensation system is adapted to correct for temperature induced variations in the pressure sensor signal, and the drift compensation system is adapted to correct for pressure and temperature induced pressure sensor signal drift.

SUMMARY OF THE INVENTION

An embodiment of the present invention that is described herein provides a method including, in a living organ in which an ambient pressure varies as a function of time, sensing the ambient pressure using a pressure sensor, which has a capacitance that varies in response to the ambient pressure, so as to produce a time-varying waveform. A calibration voltage, which modifies the capacitance and thus the time-varying waveform, is applied to the pressure sensor. The time-varying waveform is processed so as to isolate and measure a contribution of the calibration voltage to the waveform. A dependence of the capacitance on the ambient pressure is calibrated using the measured contribution of the calibration voltage.

In some embodiments, applying the calibration voltage includes automatically identifying one or more time intervals in which the waveform meets a predefined criterion, and applying the calibration voltage during the identified time intervals. In some embodiments, the ambient pressure oscillates as a function of time in accordance with a periodic cycle, and applying the calibration voltage includes activating the calibration voltage at a predefined phase of the cycle. Applying the calibration voltage may include activating the calibration voltage during a portion of the periodic cycle in which the waveform varies by less than a predefined variation. Additionally or alternatively, applying the calibration voltage may include activating the calibration voltage at the phase of the cycle in which the waveform has a predefined value.

In an embodiment, processing the waveform includes analyzing the waveform so as to automatically identify one or more times at which the calibration voltage is applied, and measuring the contribution of the calibration voltage at the automatically-identified times. In another embodiment, applying the calibration voltage includes activating the calibration voltage at one or more predefined times, and processing the waveform includes measuring the contribution by synchronizing to the predefined times.

In another embodiment, processing the waveform includes identifying one or more first times at which the calibration voltage is applied, identifying one or more second times at which the calibration voltage is not applied, and measuring the contribution of the calibration voltage by comparing the waveform at the first times to the waveform at the second times. In yet another embodiment, applying the calibration voltage includes applying at least two different calibration voltage levels. In still another embodiment, processing the waveform includes determining a level of the calibration voltage that causes the capacitance to reach a given capacitance value. In another embodiment, processing the waveform includes determining a level of the calibration voltage that triggers a discrete event related to electrodes of the pressure sensor.

There is additionally provided, in accordance with an embodiment of the present invention, a method including, in a living organ in which an ambient pressure varies as a function of time, sensing the ambient pressure using a pressure sensor, which has a capacitance that varies in response to the ambient pressure. An oscillator circuit, which is coupled to the pressure sensor, is operated such that an output of the oscillator circuit depends on the capacitance and thus varies depending on the ambient pressure. An operating point of the oscillator circuit is modified, so as to apply to the pressure sensor a calibration voltage that modifies the capacitance. A change in the output of the oscillator circuit, caused by the calibration voltage, is sensed. A dependence of the capacitance on the ambient pressure is calibrated using the sensed change.

In some embodiments, modifying the operating point includes modifying a supply voltage of the oscillator circuit. In some embodiments, operating the oscillator circuit includes adjusting a frequency of the output of the oscillator circuit as a function of the capacitance. In an embodiment, operating the oscillator circuit includes operating a Schmidt trigger that is connected in a feedback loop including the pressure sensor. In a disclosed embodiment, operating the oscillator circuit includes switching the oscillator circuit between the pressure sensor and a reference capacitance, and calibrating the dependence includes comparing first and second outputs of the oscillator circuit when connected to the pressure sensor and to the reference capacitance, respectively.

There is additionally provided, in accordance with an embodiment of the present invention, apparatus including a pressure sensor and calibration circuitry. The pressure sensor is configured to be fitted in a living organ in which an ambient pressure varies as a function of time, and to sense the ambient pressure using a capacitance that varies in response to the ambient pressure, so as to produce a time-varying waveform. The calibration circuitry is configured to apply to the pressure sensor a calibration voltage that modifies the capacitance and thus the time-varying waveform, to process the time-varying waveform so as to isolate and measure a contribution of the calibration voltage to the waveform, and to calibrate a dependence of the capacitance on the ambient pressure using the measured contribution of the calibration voltage.

There is further provided, in accordance with an embodiment of the present invention, apparatus including a pressure sensor, an oscillator circuit and calibration circuitry. The pressure sensor is configured to be fitted in a living organ in which an ambient pressure varies as a function of time, and to sense the ambient pressure using a capacitance that varies in response to the ambient pressure. The oscillator circuit is coupled to the pressure sensor and is configured to oscillate such that an output of the oscillator circuit depends on the capacitance and thus varies depending on the ambient pressure. The calibration circuitry is configured to modify an operating point of the oscillator circuit so as to apply to the pressure sensor a calibration voltage that modifies the capacitance, to sense a change in the output of the oscillator circuit caused by the calibration voltage, and to calibrate a dependence of the capacitance on the ambient pressure using the sensed change.

The present invention will be more fully understood from the following detailed description of the embodiments thereof, taken together with the drawings in which:

DETAILED DESCRIPTION OF EMBODIMENTS

Overview

Embodiments of the present invention that are described herein provide improved methods and systems for calibrating capacitance-based pressure sensors. The embodiments described herein refer mainly to measurement of blood pressure in the heart using a cardiac implant, but the disclosed techniques can be used in various other applications, as well.

The capacitance-based pressure sensor has a certain pressure-capacitance dependence, which is used for deriving the pressure from the sensor capacitance. In practice, however, the pressure-capacitance dependence of the sensor may drift considerably over time, for example due to aging of sensor elements or tissue build-up on or around the sensor. Unless calibrated and compensated for, this drift may distort the pressure estimation considerably.

The calibration task is further complicated by the fact that the measured ambient pressure is noisy and varies periodically in accordance with the patient's cardiac cycle. Thus, readout of the pressure sensor produces a noisy, time-varying waveform. The disclosed techniques calibrate the pressure-capacitance dependence of the sensor using this waveform.

In some embodiments, the implant comprises calibration circuitry that applies a calibration voltage to the pressure sensor. The calibration voltage modifies the sensor capacitance, which in turn modifies the time-varying waveform. In other words, the time-varying waveform is affected by two factors—The ambient pressure and the calibration voltage. The calibration circuitry processes the time-varying waveform so as to measure the contribution of the calibration voltage and isolate this contribution from other factors. The measured contribution of the calibration voltage is then used for calibrating the pressure-capacitance dependence of the sensor.

Several example calibration circuitry configurations are described herein. In some embodiments, the calibration voltage is applied directly to the pressure sensor electrodes. In other embodiments, the pressure sensor is coupled to an oscillator circuit, and the calibration is used to modify the operating point of the oscillator circuit, and thus indirectly modify the sensor capacitance.

Several example techniques for isolating and measuring the contribution of the calibration voltage to the time-varying waveform are described. Some of these techniques involve synchronizing to the periodic cardiac cycle and choosing suitable time intervals for applying the calibration voltage.

The disclosed techniques provide highly accurate compensation for drift in the pressure-capacitance dependence of capacitance-based pressure sensors. These techniques are particularly designed for environments in which the ambient pressure in noisy and time-varying, although they are suitable for static environments as well. The methods and systems described herein operate in real time and are entirely non-invasive. As such, they enable the pressure sensor to remain operative for years without performance degradation.

System Description

Figure 1:
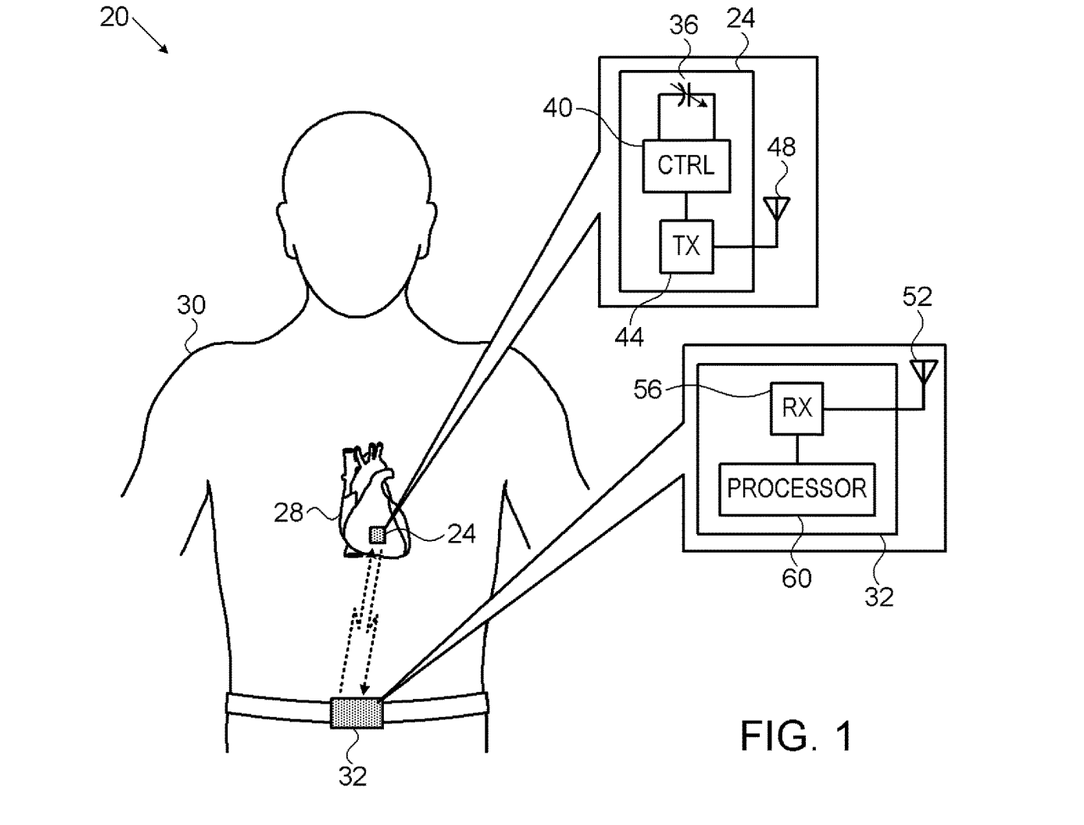
FIG. 1 is a block diagram that schematically illustrates a system for monitoring left-atrial blood pressure, in accordance with an embodiment of the present invention.

FIG. 1 is a block diagram that schematically illustrates a system 20 for monitoring left-atrial blood pressure, in accordance with an embodiment of the present invention. System 20 comprises an implant 24 that is implanted in a heart 28 of a patient 30, and an external unit 32 that is placed in proximity to the patient.

Implant 24 measures the time-varying ambient blood pressure in the Left Atrium (LA) of heart 28, and transmits a corresponding time-varying waveform to external unit 32. The external unit estimates the blood pressure based on the waveform received from implant 24 and outputs the estimated blood pressure to a user, e.g., a physician or the patient himself. In some embodiments the external unit also supplies electrical power to the implant, e.g., using inductive coupling.

In the embodiment of FIG. 1, implant 24 comprises a capacitance-based pressure sensor 36. In the present example, sensor 24 comprises a capacitor that is fabricated using Micro-Electromechanical System (MEMS) technology. One of the electrodes of this capacitor comprises a membrane that is exposed to the ambient blood pressure. The pressure applied by the blood to the membrane sets the spacing between the capacitor electrodes, and therefore sets the capacitor's capacitance. In alternative embodiments, sensor 36 may comprise any other suitable kind of sensor whose capacitance is indicative of the ambient pressure.

Implant 24 comprises a control unit 40 that controls and reads pressure sensor 36. Among other tasks, unit 40 produces a time-varying waveform that is indicative of the time-varying capacitance of sensor 36, and thus the time-varying pressure. Implant 24 further comprises a transmission unit 44 that transmits the time-varying waveform via an antenna 48 to external unit 32 for subsequent processing. In an example embodiment, unit 44 transmits a square wave whose frequency is proportional to the amplitude of the waveform (and thus to the measured pressure).

External unit 32 receives the time-varying waveform from implant 24 using an antenna 52 and a receiver 56. A processor 60 then processes the received waveform so as to estimate the actual blood pressure sensed by sensor 36. The estimated blood pressure is provided as output to a user using a suitable interface.

In some embodiments, unit 40 in conjunction with external unit 32 carries out a calibration process that compensates for drift effects in the pressure-capacitance dependence of sensor 36. This calibration process, and several example configurations of unit 40 that support such calibration, are described in detail below.

Figure 4:
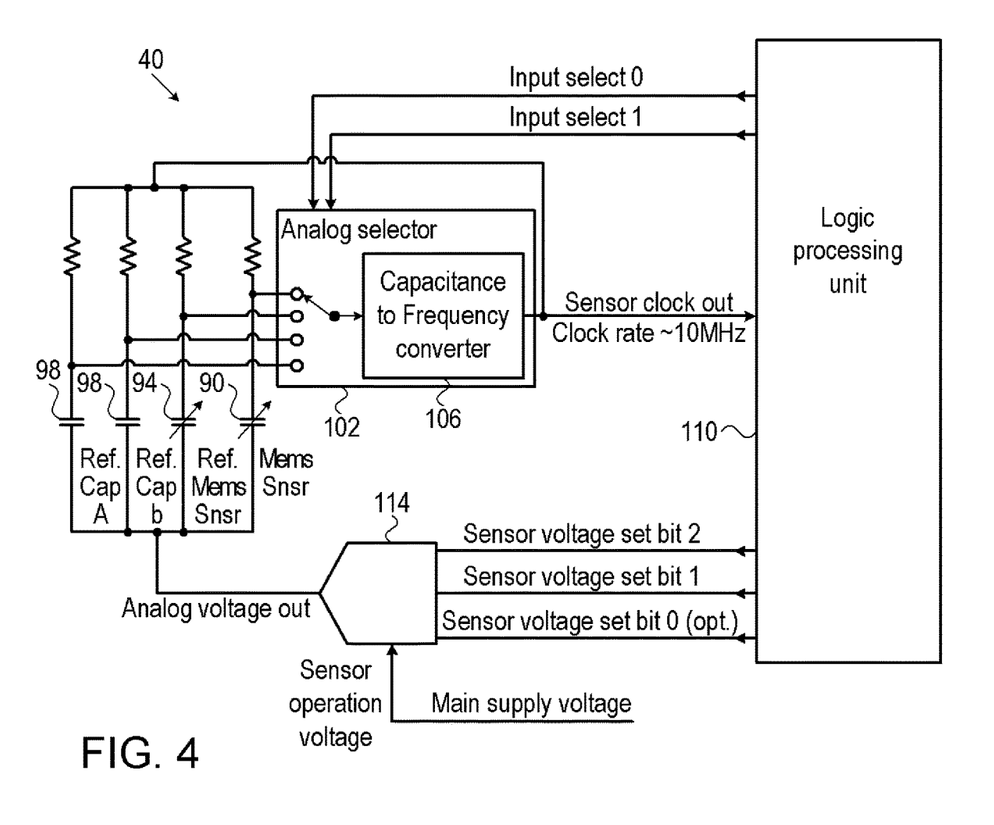
FIG. 4 is a block diagram that schematically illustrates a control unit in a cardiac implant, in accordance with an embodiment of the present invention.
Figure 6:
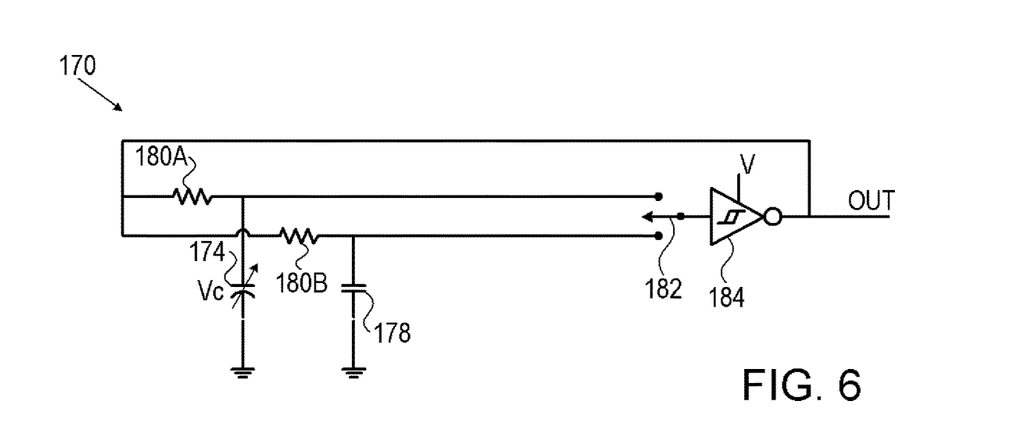
FIG. 6 is an example circuit diagram of a capacitance-to-frequency converter, in accordance with an embodiment of the present invention.

The configurations of implant 24 and external unit 32 shown in FIG. 1 are example configurations, which are chosen purely for the sake of conceptual clarity. FIGS. 4 and 6 below show example implementation schemes for elements of control unit 40. In alternative embodiments, however, any other suitable configurations can be used for implementing the implant and/or external unit.

The disclosed calibration techniques can be carried out by control unit 40 in implant 24, by processor 60 in external unit 32, or by both. In the context of the present patent application and in the claims, the elements of unit 40 and/or processor 60 that carry out calibration tasks are referred to collectively as "calibration circuitry." Elements of the implant and/or the external unit that are not necessary for understanding of the disclosed techniques have been omitted from the figures for the sake of clarity.

The various elements of implant 24 and external unit 32 can be implemented using hardware, such as using an Application Specific Integrated Circuit (ASIC) or Field Programmable Gate Array (FPGA), using software, or using a combination of hardware and software elements. In some embodiments, elements of implant 24 and/or external unit 32 are implemented using a general-purpose processor, which is programmed in software to carry out the functions described herein. The software may be downloaded to the processor in electronic form, over a network, for example, or it may, alternatively or additionally, be provided and/or stored on non-transitory tangible media, such as magnetic, optical, or electronic memory.

Drift Effects in Capacitance-Based Pressure Sensor

System 20 measures the ambient blood pressure in heart 28 by assessing the capacitance of sensor 36. The underlying assumption is that the capacitance varies as a function of the pressure in accordance with some known dependence, which is then used for deriving the pressure from the measured capacitance.

In practice, however, the dependence of the sensor capacitance on the ambient pressure drifts over time. For example, the dependence may follow a certain function immediately after a new implant 24 is implanted in heart 28, but drift to follow a different function several months later. This drift may be caused, for example, by a change in the mass or stiffness of the sensor membrane, by growth or deposition of biological tissue on the sensor or in its vicinity, or by various other mechanisms.

Figure 2:
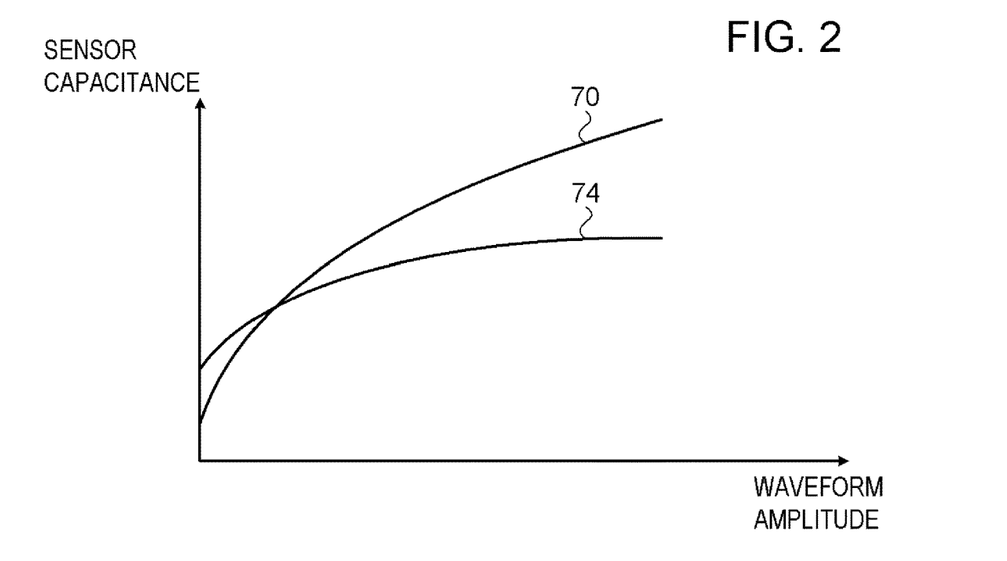
FIG. 2 is a graph that schematically illustrates a drift effect in a capacitance-based pressure sensor, in accordance with an embodiment of the present invention.

FIG. 2 is a graph that schematically illustrates a drift effect in capacitance-based pressure sensor 36, in accordance with an embodiment of the present invention. A curve 70 shows the pressure-capacitance dependence of sensor 36 immediately after implantation in the heart. A curve 74 shows the pressure-capacitance dependence several months or years after implantation. As can be seen in the figure, there is considerable drift between the two curves. Unless accounted for, drift of this sort may considerably degrade the pressure estimation accuracy of system 20.

The problem of calibrating the drift is further complicated by the fact that the measured pressure is not constant, but rather noisy and time-varying in accordance with the patient's cardiac cycle.

Figure 3:
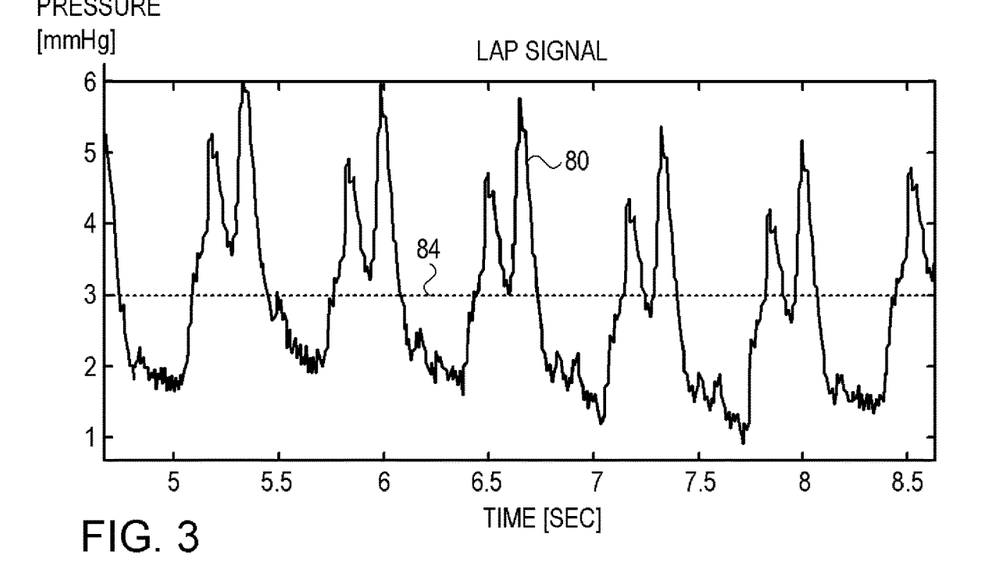
FIG. 3 is a graph showing time-varying blood pressure measured by a capacitance-based pressure sensor, in accordance with an embodiment of the present invention.

FIG. 3 is a graph showing an example of time-varying blood pressure measured by pressure sensor 36, in accordance with an embodiment of the present invention. A curve 80 shows the blood pressure as a function of time, sampled at a rate of 1 KHz. As can be seen in the figure, the blood pressure oscillates in a periodic pattern in accordance with the cardiac cycle, and also comprises considerable measurement noise. The capacitance of sensor 36, and thus the waveform produced by the implant, varies in time accordingly. As can be appreciated, calibrating drift over such a waveform is considerably more complicated than calibrating over a constant pressure measurement.

Example Drift Calibration Schemes

In some embodiments, the calibration circuitry in system 20 calibrates the drift in the pressure-capacitance dependence by applying a calibration voltage to sensor 36. The applied calibration voltage causes additional deflection of the sensor's membrane. The total deflection of the membrane is thus affected by two factors—The ambient blood pressure, and the calibration voltage.

Put in another way (since capacitance depends on membrane deflection), readout of sensor 36 produces a time-varying waveform that depends on two factors—The ambient blood pressure, and the calibration voltage. Typically, the calibration circuitry processes the waveform so as to distinguish between the two factors, i.e., to isolate the contribution of the calibration voltage to the time-varying waveform. The calibration circuitry then uses the isolated contribution of the calibration voltage to calibrate the drift in pressure-capacitance dependence of sensor 36.

FIG. 4 is a block diagram that schematically illustrates elements of control unit 40 of implant 36, in accordance with an embodiment of the present invention. In the embodiment of FIG. 4, unit 40 reads a MEMS capacitance-based pressure sensor 90 in order to measure the ambient blood pressure.

In this example, the implant further comprises a reference capacitance-based sensor 94 and two fixed capacitors 98, all serving as reference capacitances. Reference sensor 94 is typically similar to sensor 90. Unlike sensor 90, however, sensor 94 is not exposed to the blood, and can therefore be used for obtaining reference measurements. Capacitors 98 typically have different known values within the capacitance range of sensor 90. A logic unit 110 in control unit 40 selects between the outputs of the four capacitors using a selector switch 102.

In an embodiment, unit 40 comprises a capacitance-to-frequency converter 106, which produces a waveform whose frequency is indicative of the capacitance of the selected capacitor. In the present example, converter 106 produces a square-wave clock signal (denoted "sensor clock out" in the figure) whose frequency is around 10 MHz. The exact frequency of the clock signal depends on the measured capacitance. The waveform is provided to logic unit 110. Subsequent processing of the signal (e.g., transmission to external unit 32 and calibration using the signal) are not shown in this figure for the sake of clarity.

Unit 40 comprises an operation voltage module 114, which applies an appropriate calibration voltage to one of the electrodes of the pressure sensor (sensor 90 or 94). In the present example, unit 110 selects the calibration voltage with a resolution of two or three bits, by controlling module 114 using suitable control signals. Module 114 generates the desired voltage levels from the main supply voltage of unit 40.

The scheme of FIG. 4 is depicted purely by way of example. In alternative embodiments, unit 40 may apply the calibration voltage to the pressure sensor in any other suitable way. An alternative scheme, in which the calibration voltage is applied indirectly by changing an operating point of an oscillator whose frequency depends on the sensor capacitance, is shown in FIG. 6 below.

Isolating the Contribution of the Calibration Voltage to the Sensor Capacitance

As explained above, the capacitance of the pressure sensor depends on (1) the ambient pressure and (2) the calibration voltage. The ambient pressure is typically both time-varying and noisy. In order to perform accurate drift compensation, system 20 processes the noisy, time-varying waveform produced from the pressure sensor, and isolates the contribution of the calibration sensor from the other factors.

System 20 may isolate the contribution of the calibration voltage in various ways. In some embodiments, system 20 applies the calibration voltage only is selected time intervals that meet some predefined criterion. Such intervals are typically selected in a particular phase of the cardiac cycle. For example, the system may activate the calibration voltage only in phases of the cardiac cycle in which the waveform amplitude varies by less than a predefined variation. In such intervals it is simpler to measure the contribution of the calibration voltage than in rapidly-varying portions of the cardiac cycle.

Figure 5:
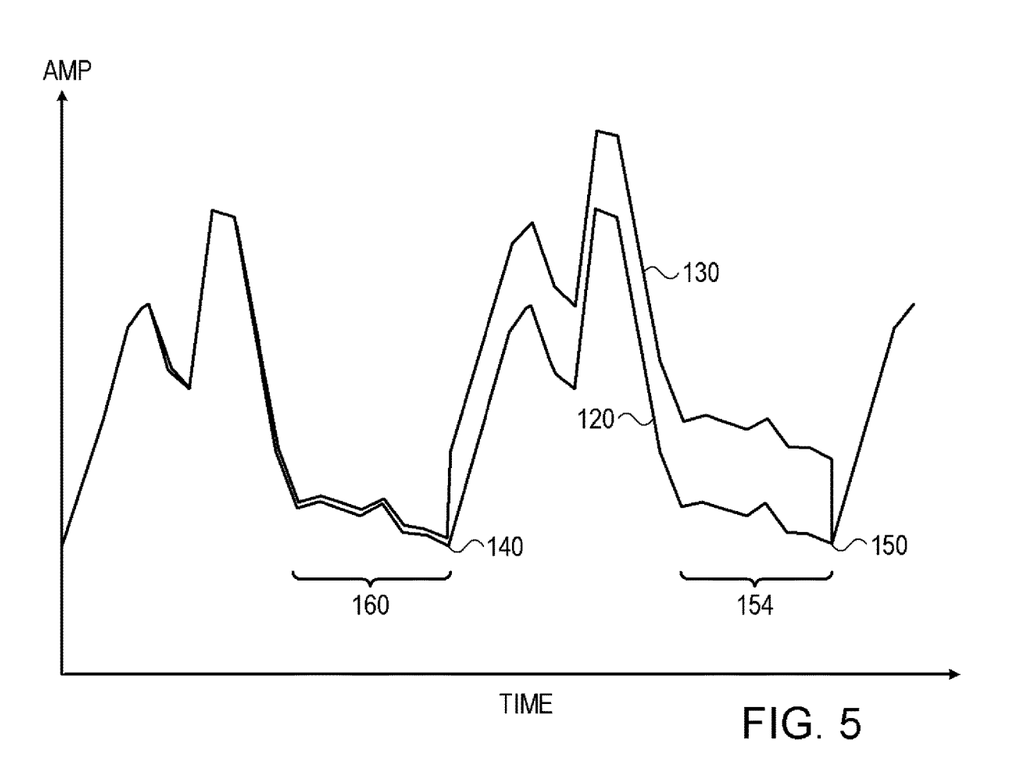
FIG. 5 is a graph showing the effect of applying a calibration voltage to a capacitance-based pressure sensor, in accordance with an embodiment of the present invention.

FIG. 5 is a graph showing the effect of applying a calibration voltage to a capacitance-based pressure sensor, in accordance with an embodiment of the present invention. The graph shows a simulation of the amplitude of the time-varying waveform produced by reading the pressure sensor over two cardiac cycle periods.

A curve 120 shows the waveform amplitude without applying any calibration voltage. A curve 130 shows the waveform amplitude when a calibration voltage is applied between times 140 and 150 (i.e., activated at time 140 and deactivated at time 150). As can be seen in the figure, during slowly-varying intervals of the cardiac cycle, such as an interval 154, it is relatively simple to measure the contribution of the calibration voltage to the waveform amplitude, whereas in rapidly-varying intervals this task is more complicated and less accurate.

In an example embodiment, system 20 measures the contribution of the calibration voltage by comparing one or more time intervals in which the calibration voltage is applied to corresponding intervals in which the calibration voltage is not applied. In the example of FIG. 5, system 20 may compare the amplitude in interval 154 (in which the calibration voltage is applied) to the amplitude in a corresponding interval 160 (at the same phase of the cycle in another cycle period, in which the calibration voltage is not applied). The average difference between these amplitudes is indicative of the contribution of the calibration voltage to the waveform amplitude.

In some embodiments, system 20 averages the above-described measurement over multiple cardiac cycles, in order to reduce the effect of noise and generally improve the measurement accuracy. In some embodiments, system 20 identifies automatically the intervals in which the calibration voltage is applied and the intervals in which the calibration voltage is not applied, in order to perform the above-described comparison.

In some embodiments, system 20 automatically synchronizes to the patient's cardiac cycle and identifies the time intervals that meet the desired criterion (e.g., intervals of slowly-varying waveform). System 20 then applies the calibration voltage in at least some of these intervals (while potentially leaving some of the intervals free of calibration voltage for comparison), and calculates the isolated contribution of the calibration voltage from the waveform amplitude in the intervals.

In alternative embodiments, system 20 activates the calibration voltage at the phase of the cardiac cycle in which the waveform has a predefined value. This technique is another possibility for synchronizing to the timing of the cardiac cycle and applying the calibration voltage at a desired phase of the cycle.

In another embodiment, system 20 applies multiple calibration voltages. This sort of calibration may enable highly accurate isolation of the contribution of the calibration voltage to the waveform amplitude. The system may apply the calibration voltage or voltages without necessarily synchronizing to the cardiac cycle. For example, the system may apply multiple voltages at specific times that are not correlated to the ambient pressure or to the cardiac cycle. In an example embodiment, a first voltage is applied three seconds after starting operation, a second voltage is applied six seconds after starting operation, and a third voltage is applied eight seconds after starting operation. In such a scheme, each calibration voltage will typically be applied over several cardiac cycles.

In other embodiments, system 20 identifies the calibration voltage value that is needed in order to set a predefined capacitance value. In some embodiments, system 20 applies a gradually-increasing calibration voltage, and finds the calibration voltage value that causes some discrete detectable event relating to the electrodes of the pressure sensor. For example, system 20 may find the calibration voltage value that corresponds to the "touch point"—The voltage that causes the sensor electrodes to make physical contact with each other.

As another example, system 20 may find the calibration voltage value that corresponds to the "pull-in" point. Pull-in is an effect in which the sensor membrane collapses toward the other electrode. This discrete event can be detected, for example, by detecting both a certain voltage-capacitance relation and a rapid change in current. Upon detecting such an event, system 20 is able to deduce the contribution of the calibration voltage, for example by comparing the measurement to baseline measurements taken at known conditions. Further alternatively, system 20 may identify any other suitable discrete event that is caused by some threshold calibration voltage.

Typically, the calibration process is performed jointly by control unit 40 in implant 24 and by processor 60 in external unit 32. In an example embodiment, the criteria and timing for applying the calibration voltage are determined and carried out internally in implant 24, and the direction of communication between implant 24 and external unit 32 is unidirectional (from the implant to the external unit). In other embodiments, the communication between the implant and the external unit may be bidirectional. In some embodiments, control unit 40 and processor 60 are synchronized with one another as to the times at which the calibration voltage is applied. The schemes described above are chosen purely by way of example. Alternatively, system 20 may isolate the contribution of the calibration voltage to the amplitude of the time-varying waveform in any other suitable way.

Indirect Application of Calibration Voltage During Capacitance-to-Frequency Conversion In the scheme of FIG. 4 above, control unit 40 applies the calibration voltage directly to one of the electrodes of the capacitance-based pressure sensor. In alternative embodiments, the calibration voltage is applied indirectly: The pressure sensor is part of an oscillator circuit whose operating point is set by the calibration voltage.

Consider, for example, capacitance-to-frequency converter 106 of FIG. 4. In some embodiments, unit 40 modifies the operating point of converter 106 using the calibration voltage, instead of applying the calibration voltage to the pressure sensor directly. Modifying the operating point causes a modification of the voltage that falls on the pressure sensor, and thus achieves the desired goal of changing the sensor capacitance.

FIG. 6 in an example circuit diagram of a capacitance-to-frequency converter 170, in accordance with an embodiment of the present invention. This circuit can be used to implement converter 106 of FIG. 4. In converter 170, a capacitance-based pressure sensor 174 is coupled to an oscillator circuit, such that the capacitance of sensor 174 sets the oscillation frequency.

In the present example, the oscillator circuit comprises a Schmidt trigger 184 that is connected in a feedback loop that comprises a resistor 180A. The output of Schmidt trigger 184 (denoted "OUT" in the figure) comprises a square wave whose frequency depends on the capacitance of sensor 174.

In some embodiments, unit 40 applies the calibration voltage as the supply voltage (denoted "V") of Schmidt trigger 184. Changing the supply voltage V causes a respective change in the voltage falling on sensor 74 (denoted "Vc"), and thus changes the sensor capacitance.

In the present example, converter 170 comprises a fixed capacitor 178 and a resistor 180B, used as reference. Selection between pressure sensor 174 and capacitor 178 is performed using a switch 182. In some embodiments, the system calibrates the capacitance-pressure dependence of sensor 174 by comparing the respective outputs of converter 170 when connected to pressure sensor 174 and when connected to capacitor 178.

Figure 7:
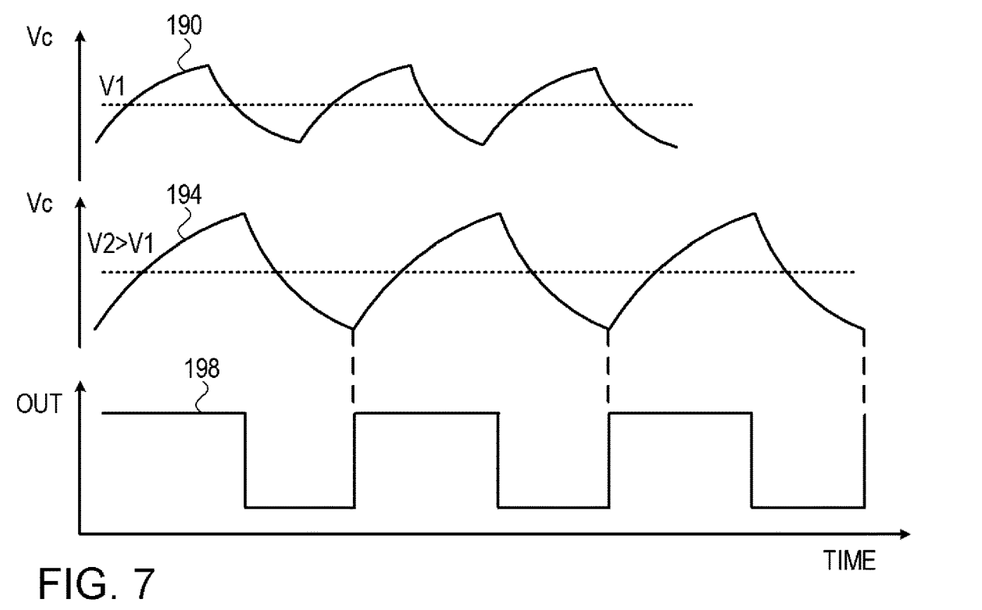
FIG. 7 is a graph showing waveforms in the capacitance-to-frequency converter of FIG. 6, in accordance with an embodiment of the present invention.

FIG. 7 is a graph showing waveforms in capacitance-to-frequency converter 170 of FIG. 6, in accordance with an embodiment of the present invention. A curve 190 shows the voltage Vc on pressure sensor 174 when the calibration voltage (and thus the supply voltage of Schmidt trigger 184) is set to some value V1. A curve 194 shows the voltage Vc on pressure sensor 174 when the calibration voltage is set to another value V2, V2>V1. A curve 198 shows the square-wave output of converter 170 produced for calibration voltage V2.

As can be seen in the figure, increasing the calibration voltage causes a reduction in the oscillation frequency, and vice versa. Since the oscillation frequency is relatively high (e.g., on the order of 10 MHz), the capacitance of sensor 174 is responsive to the average value of Vc (marked with dashed lines) and not to the instantaneous oscillating value.

Thus, the frequency of the output of converter 170 depends on two factors—The capacitance of sensor 174 and the calibration voltage. Thus, the equivalent effect of the calibration voltage is achieved by using the calibration voltage to modify the capacitance-frequency dependence of converter 170.

In the scheme of FIGS. 6 and 7, selection of activation times for the calibration voltage and isolation of the contribution of the calibration voltage can be performed in accordance with the criteria defined in the "Isolating the contribution of the calibration voltage to the sensor capacitance" section above.

Calibration Method Description

Figure 8:
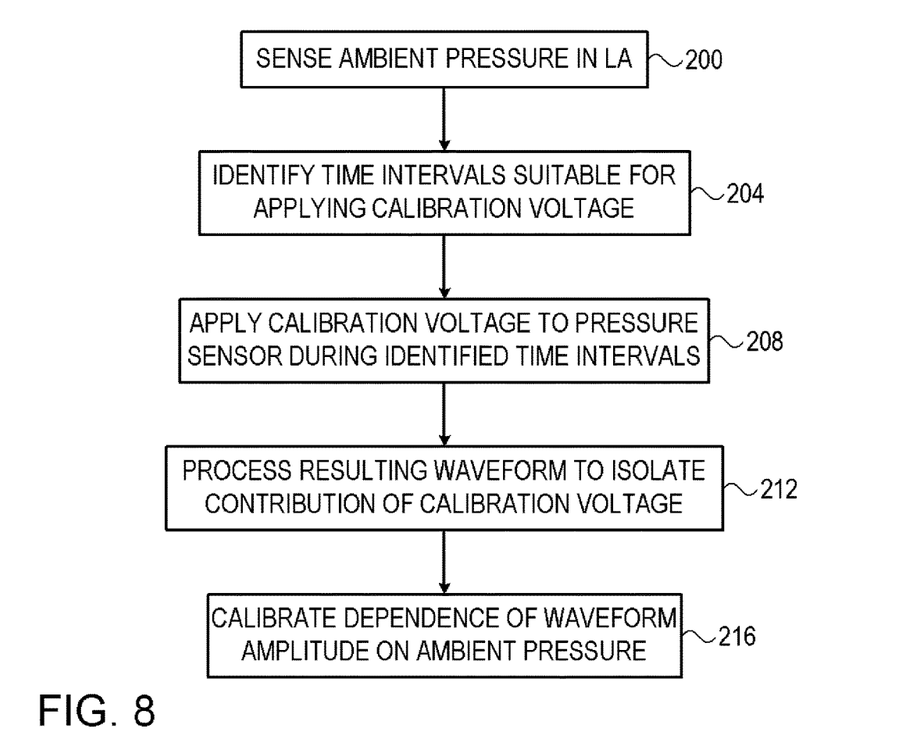
FIG. 8 is a flow chart that schematically illustrates a method for calibrating a capacitance-to-frequency converter, in accordance with an embodiment of the present invention.

FIG. 8 is a flow chart that schematically illustrates a method for calibrating a capacitance-to-frequency converter, in accordance with an embodiment of the present invention. The method begins with the capacitance-based pressure sensor sensing the ambient pressure in the patient's LA, at a sensing step 200. System 20 identifies time intervals that are suitable for applying the calibration voltage, at an interval identification step 204. System 20 applies the calibration voltage during at least some of the identified time intervals, at a voltage application step 208. In some embodiments, multiple voltage levels are applied. In an example embodiment, the system applies four different calibration voltages at predefined times.

System 20 processes the resulting time-varying waveform, at an analysis step 212. In particular, system 20 isolates the contribution of the calibration voltage to the waveform from other factors. Using the isolated contribution of the calibration voltage, system 20 calibrates the pressure-capacitance dependence of the sensor, at a calibration step 216.

Additional Capacitance-to-Frequency Converter Configurations

Figure 9:
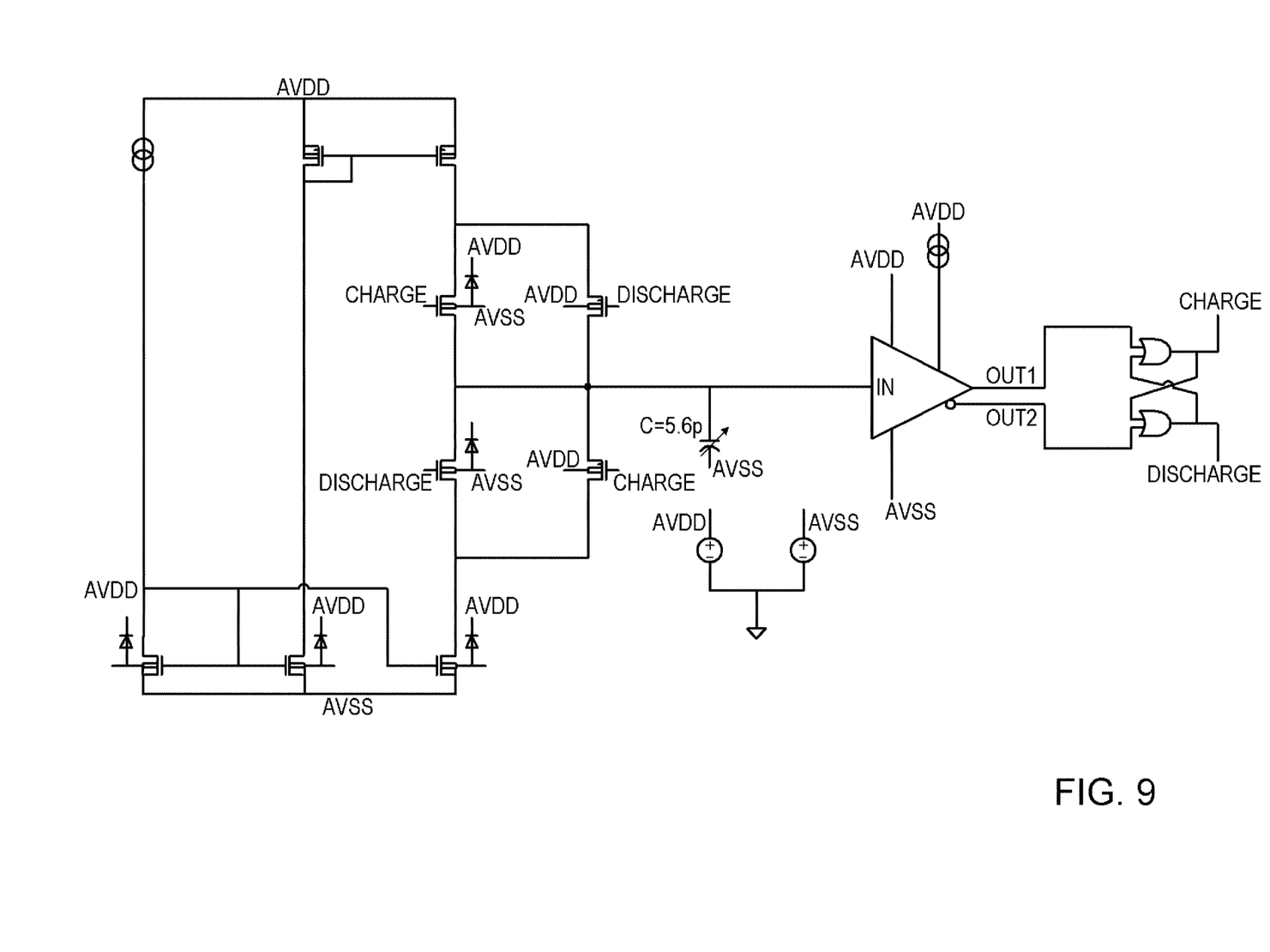
FIGS. 9 and 10 are example circuit diagrams of capacitance-to-frequency converters, in accordance with embodiments of the present invention.
Figure 10:
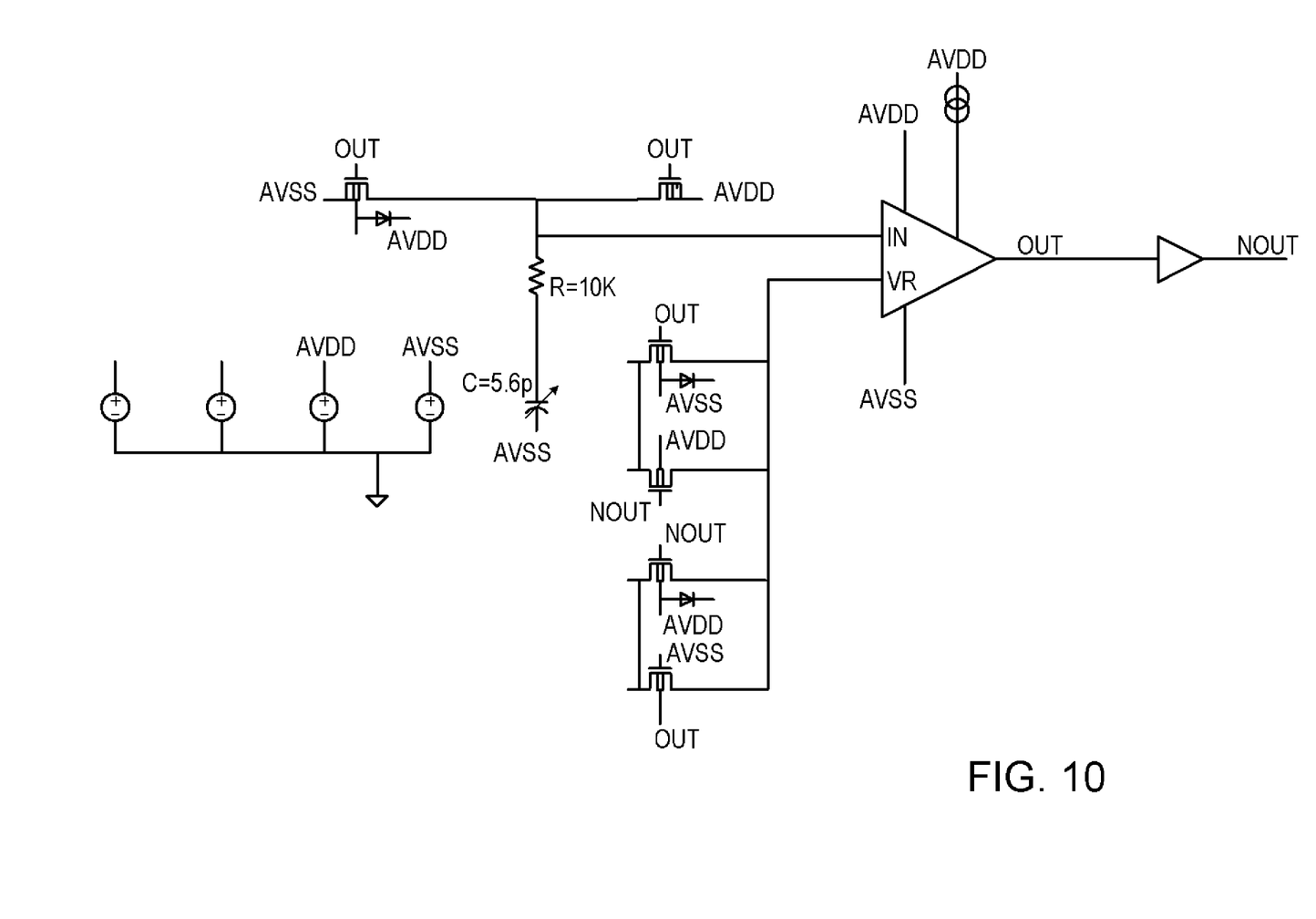

FIGS. 9 and 10 are example simulated circuit diagrams of capacitance-to-frequency converters, in accordance with embodiments of the present invention. These circuits can be used for implementing capacitance-to-frequency converter 106 of FIG. 4 above. In both figures, the capacitance-based pressure sensor is modeled by the variable capacitor denoted C=5.6 pF. In both circuits, the static voltage over the capacitance-based pressure sensor is changed by changing the "AVSS" voltage on one of the pressure sensor electrodes.

FIG. 9 describes a current-mode configuration, in which constant current either charges or discharges the capacitor according to the oscillator output state. The AC voltage shape across the 5.6 pF capacitor is a saw tooth. FIG. 10 describes a voltage-mode configuration. In this circuit, the 5.6 pF capacitor is charged/discharged exponentially via the 10K ohm resistor. Hysteresis is obtained by toggling the voltage on the VR input of the comparator.

Although the embodiments described herein mainly address measurement of ambient blood pressure in the LA, the methods and systems described herein can also be used in other applications, such as in other cardiac chambers or in other body organs.

For example, the disclosed techniques can be used for measuring blood pressure in the Aorta, renal artery, femoral artery or radial artery, e.g., for better management of hypertension patients. As another example, the disclosed techniques can be used for measuring pulmonary artery pressure for better management of heart failure patients. As yet another example, the disclosed techniques can be used for intracranial pressure (ICP) monitoring which can aid in the management of neurological disorders such as hydrocephalus, head trauma, tumors, colloid cysts and cerebral hematomas.

In another example embodiment, the disclosed techniques can be used for bladder pressure monitoring, e.g., as a diagnostic tool for urology. The disclosed techniques may also be used for intraocular pressure (IOP) monitoring for better treatment of glaucoma. Moreover, intra-cardiac pressure monitoring using the disclosed techniques can also be used as a complementary technology for ventricular assist devices (VAD) and CRT optimization.

Alternatively to measuring blood pressure, the disclosed techniques can be used in measurements of pressure in other liquids, in gases or in solids. Although the embodiments described herein refer mainly to an implanted device that operates in conjunction with an external unit, the disclosed techniques can be used in pressure sensors coupled to other kinds of medical devices, such as catheters or other probes.

It will thus be appreciated that the embodiments described above are cited by way of example, and that the present invention is not limited to what has been particularly shown and described hereinabove. Rather, the scope of the present invention includes both combinations and sub-combinations of the various features described hereinabove, as well as variations and modifications thereof which would occur to persons skilled in the art upon reading the foregoing description and which are not disclosed in the prior art. Documents incorporated by reference in the present patent application are to be considered an integral part of the application except that to the extent any terms are defined in these incorporated documents in a manner that conflicts with the definitions made explicitly or implicitly in the present specification, only the definitions in the present specification should be considered.

The invention claimed is:
1. A method for ambient pressure measurement, the method comprising:
sensing, in a heart of a patient, a time-varying ambient pressure that varies in accordance with a cardiac cycle of the heart, using a pressure sensor having a capacitance that varies depending on the time-varying ambient pressure, so as to produce a sensor-output waveform that also varies in accordance with the cardiac cycle;
while the pressure sensor is measuring the time-varying ambient pressure in the heart, intermittently applying to the pressure sensor a calibration voltage, which further contributes to the capacitance in addition to a contribution of the time-varying ambient pressure;
automatically identifying one or more first time-intervals in which the calibration voltage was applied and one or more second time-intervals in which the calibration voltage was not applied;
comparing the sensor-output waveform during the one or more first time-intervals to the sensor-output waveform during the one or more second time-intervals, to determine a difference between the sensed pressure in the first and second time-intervals;
calibrating a dependence of the capacitance on the ambient pressure, based on the applied calibration voltage and the corresponding determined difference between the sensed pressure in the first and second time-intervals; and outputting an output indicative of a calibrated ambient pressure, based on the calibrated dependence.

2. The method according to claim 1, wherein intermittently applying the calibration voltage comprises applying the calibration voltage at a predefined phase of the cardiac cycle.

3. The method according to claim 2, wherein intermittently applying the calibration voltage comprises applying the calibration voltage during a portion of the cardiac cycle in which the sensor-output waveform varies by less than a predefined variation.

4. The method according to claim 2, wherein intermittently applying the calibration voltage comprises applying the calibration voltage at the phase of the cardiac cycle in which the sensor-output waveform has a predefined value.

5. The method according to claim 1, wherein automatically identifying the one or more first time-intervals comprises analyzing the sensor-output waveform so as to automatically identify the one or more first time intervals in which the calibration voltage is applied.

6. The method according to claim 1, wherein applying the calibration voltage comprises applying at least two different calibration voltage levels.

7. The method according to claim 1, further comprising determining a level of the calibration voltage that causes the capacitance to reach a given capacitance value.

8. The method according to claim 1, further comprising determining a level of the calibration voltage that triggers a discrete event related to electrodes of the pressure sensor.

9. The method according to claim 1, wherein identifying the first and second time-intervals comprises selecting time intervals in which the sensor-output waveform varies by less than a predefined variation.

10. The method according to claim 1, wherein identifying the first and second time-intervals comprises selecting time-intervals of a particular phase of the cardiac cycle.

11. The method according to claim 1, wherein comparing the sensor-output waveform during the first and second time-intervals comprises calculating an average difference between an amplitude of the first time-intervals and an amplitude of the second time-intervals.

12. The method according to claim 1, wherein the first one or more time-intervals comprise a plurality of first time intervals included in multiple cardiac cycles.

13. The method according to claim 1, wherein applying the calibration voltage comprises modifying an operating point of a capacitance-to-frequency converter which produces a waveform whose frequency is indicative of the capacitance of the pressure sensor.

14. The method according to claim 1, wherein intermittently applying the calibration voltage comprises applying the calibration voltage without synchronizing to the cardiac cycle.

15. The method according to claim 1, wherein intermittently applying the calibration voltage comprises applying the calibration voltage at times that are not correlated to the cardiac cycle.

16. The method according to claim 1, wherein intermittently applying the calibration voltage comprises applying multiple calibration voltages, each calibration voltage being applied for a period spanning over multiple the cardiac cycles.

17. The method according to claim 1, wherein intermittently applying the calibration voltage comprises synchronizing to the cardiac cycle, identifying time intervals in which the sensor-output waveform is expected to have only small variations and applying the calibration voltage to some of the identified time intervals leaving others of the identified time intervals without applying the calibration voltage.

18. An apparatus for ambient pressure measurement, the apparatus comprising:

a pressure sensor, which is configured to be fitted in a heart of a patient, and to sense in the heart a time-varying ambient pressure that varies in accordance with a cardiac cycle of the heart, the pressure sensor having a capacitance that varies depending on the time-varying ambient pressure, so as to produce a sensor-output waveform that also varies in accordance with the cardiac cycle;

an integrated circuit (IC), which is coupled to the pressure sensor and in configured to intermittently apply to the pressure sensor, while the pressure sensor is measuring the time-varying ambient pressure in the heart, a calibration voltage that further contributes to the capacitance in addition to a contribution of the time-varying ambient pressure; and a processor, which is configured to:
  automatically identify one or more first time-intervals in which the calibration voltage was applied and one or more second time-intervals in which the calibration voltage was not applied:
  compare the sensor-output waveform during the one or more first time-intervals to the sensor-output waveform during the one or more second time-intervals, to determine a difference between the sensed pressure in the first and second time-intervals;
  calibrate a dependence of the capacitance on the ambient pressure, based on the applied calibration voltage and the corresponding determined difference between the sensed pressure in the first and second time-intervals; and
  output an output indicative of a calibrated ambient pressure, based on the calibrated dependence.

19. The apparatus according to claim 18, wherein the IC is configured to apply the calibration voltage at a predefined phase of the cardiac cycle.

20. The apparatus according to claim 19, wherein the IC is configured to apply the calibration voltage during a portion of the cardiac cycle in which the sensor-output waveform varies by less than a predefined variation.

21. The apparatus according to claim 19, wherein the IC is configured to apply the calibration voltage at the phase of the cardiac cycle in which the sensor-output waveform has a predefined value.

22. The apparatus according to claim 18, wherein the processor is configured to analyze the sensor-output waveform so as to automatically identify the one or more first time intervals in which the calibration voltage is applied.

23. The apparatus according to claim 18, wherein the IC is configured to apply the calibration voltage at one or more predefined times, and wherein the processor is external to the organ and is configured to measure the contribution by synchronizing to the predefined time.

24. The apparatus according to claim 18, wherein the IC is configured to apply at least two different calibration voltage levels.

25. The apparatus according to claim 18, wherein the processor is configured to determine a level of the calibration voltage that causes the capacitance to reach a given capacitance value.

26. The apparatus according to claim 18, wherein the processor is configured to determine a level of the calibration voltage that triggers a discrete event related to electrodes of the pressure sensor.

27. The apparatus according to claim 18, wherein the first and second time intervals used in the comparison are selected as time intervals in which the sensor-output waveform varies by less than a predefined variation.

28. The apparatus according to claim 18, wherein the first and second time-intervals used in the comparison are selected as time-intervals of a particular phase of the cardiac cycle.

29. The apparatus according to claim 18, wherein the processor is configured to compare the sensor-output waveform during the first and second time-intervals by calculating an average difference between an amplitude of the first time-intervals and an amplitude of the second time-intervals.

30. The apparatus according to claim 18, wherein the first one or more time- intervals comprises a plurality of first time intervals included in multiple cardiac cycles.

31. The apparatus according to claim 18, wherein the IC is configured to apply the calibration voltage by modifying an operating point of a capacitance-to-frequency converter which produces a waveform whose frequency is indicative of the capacitance of the pressure sensor.

\* \* \* \* \*